United States Patent [19]

Spector

[11] Patent Number: 5,007,529
[45] Date of Patent: Apr. 16, 1991

[54] MICROWAVE-HEATABLE AIR-FRESHENER PACKAGE

[76] Inventor: Donald Spector, 380 Mountain Rd., Union City, N.J. 07087

[21] Appl. No.: 452,052

[22] Filed: Dec. 18, 1989

[51] Int. Cl.$^5$ .......................... A61L 9/02; A24F 25/00; F16G 13/00; F16G 11/00
[52] U.S. Cl. .................................... 206/0.5; 206/0.7; 239/53; 239/59
[58] Field of Search .................... 239/53, 55, 56, 57, 239/58, 59, 60; 206/0.5, 0.7

[56] References Cited

U.S. PATENT DOCUMENTS

| | | | |
|---|---|---|---|
| 2,609,230 | 9/1952 | Raleigh | 239/59 X |
| 2,765,194 | 10/1956 | Will | 239/59 |
| 4,258,004 | 3/1981 | Valenzona et al. | 239/59 X |
| 4,374,571 | 2/1983 | Hirvela | 206/0.5 |
| 4,544,592 | 10/1985 | Spector | 239/56 X |
| 4,664,312 | 5/1987 | Bryson | 206/0.5 |
| 4,816,659 | 3/1989 | Turko et al. | 206/0.7 |

FOREIGN PATENT DOCUMENTS

| | | | |
|---|---|---|---|
| 3332525 | 3/1984 | Fed. Rep. of Germany | 239/56 |
| 964436 | 1/1950 | France | 206/0.5 |
| 22396 | 10/1904 | United Kingdom | 206/0.5 |
| 2060392 | 5/1981 | United Kingdom | 239/53 |

Primary Examiner—William I. Price
Attorney, Agent, or Firm—Michael Ebert

[57] ABSTRACT

An air-freshener package activated by microwave energy to discharge into the atmosphere an aromatic vapor comparable to that exuded by a potpourri. The package comprises a container formed of thermal insulation material permeable to microwave energy and having a vent therein. Stored in the package is a porous pad impregnated with a liquid fragrance which simulates the aroma of a natural potpourri. When the package is irradiated in a microwave oven, the liquid fragrance is then heated to a level causing it to volatilize to generate an aromatic vapor. This vapor is discharged into the atmosphere through the vent when the package is removed from the oven and placed in a room. The temperature level is substantially maintained for a protracted period by the thermal insulation so that the aromatic vapor suffuses the room.

7 Claims, 1 Drawing Sheet

MICROWAVE OVEN

MICROWAVE-HEATABLE AIR-FRESHENER PACKAGE

BACKGROUND OF INVENTION

1. Field of Invention

This invention relates generally to a potpourri for scenting the atmosphere, and more particularly to an air-freshener package which is activated when irradiated in a microwave oven, and which remains in an activated state for a prolonged period when removed from the oven and placed in a room to discharge an aromatic vapor into the room simulating that of a natural potpourri.

2. Status of Prior Art

A traditional potpourri which exudes fragrant scents is a mixture of aromatic herbs, dried flowers and spices blended with essential oils. A traditional potpourri is usually stored in a jar, a bowl or a basket which is placed in a kitchen, bedroom or bathroom to mask unpleasant odors.

A potpourri is passive in the sense that the volume of fragrance and the rate at which it is emitted depends on the prevailing ambient temperature and humidity in the room in which it is placed. It is not too effective in scenting a large room or in doing so for more than a day or two before it is exhausted. One can reactivate a traditional potpourri by tossing its ingredients in a fragrance oil, but this is a messy procedure.

In order to accelerate the action of a potpourri, it is known to provide porous packets similar to a tea bag, containing a pulverized potpourri. The potpourri packet is simmered in a pot of boiling water to generate an aromatic vapor which fills the room in which the pot is placed.

A simmering potpourri is effective only as long as it remains in boiling water. Hence its use is usually limited to a kitchen environment. Also, one must maintain a watch on the level of the boiling water and keep children away from the pot. And since the packet releases oil into the boiling water, should the oily water spatter out of the pot, it could stain or burn nearby objects.

The complex fragrance emitted by a potpourri is such that it not only serves to mask unpleasant odors but also to suffuse the environment with a pleasing aroma that evokes a bouquet of diverse flowers rather than a single flower. As is now well known, a pleasing aroma functions as a mood modifier and acts on individuals exposed thereto to lift their depression or to make them more alert.

But existing potpourris, whether of the traditional or of the simmering type, have various practical disadvantages. Either they are incapable of generating sufficient aroma to modify an environment, or if they are capable of doing so, as with the simmering potpourri, their use is limited to a room having a heating facility.

SUMMARY OF INVENTION

In view of the foregoing, the main object of this invention is to provide a micro-wave heatable air-freshener package adapted to generate an aromatic vapor simulating that of a natural potpourri.

More particularly, an object of the invention is to provide a package of the above type which is activated in a microwave oven, and which when removed from the oven and placed in any desired environment, then acts to generate an aromatic vapor for a prolonged period.

A significant advantage of the invention is that the aroma generator may be effectively shuttered, so that if one desires to reduce the emission of aromatic vapor or shut it off entirely, this can readily be done.

Briefly stated, these objects are attained in an an air-freshener package activated by microwave energy to discharge into the atmosphere an aromatic vapor comparable to that exuded by a potpourri. The package comprises a container formed of thermal insulation material permeable to microwave energy and having a vent therein. Stored in the package is a porous pad impregnated with a liquid fragrance which simulates the aroma of a natural potpourri. When the package is irradiated in a microwave oven, the liquid fragrance is then heated to a level causing it to volatilize to generate an aromatic vapor. This vapor is discharged into the atmosphere through the vent when the package is removed from the oven and placed in a room. The temperature level is substantially maintained for a protracted period by the thermal insulation so that the aromatic vapor suffuses the room.

BRIEF DESCRIPTION OF DRAWINGS

For a better understanding of the invention as well as other objects and further features thereof, reference is made to the following detailed description to be read in conjunction with the accompanying drawings, wherein.

DESCRIPTION OF INVENTION

Figure 1:
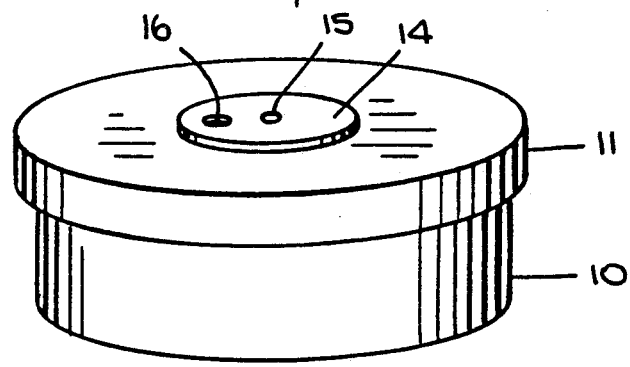
FIG. 1 is a perspective view of an air-freshener package in accordance with the invention.
Figure 2:
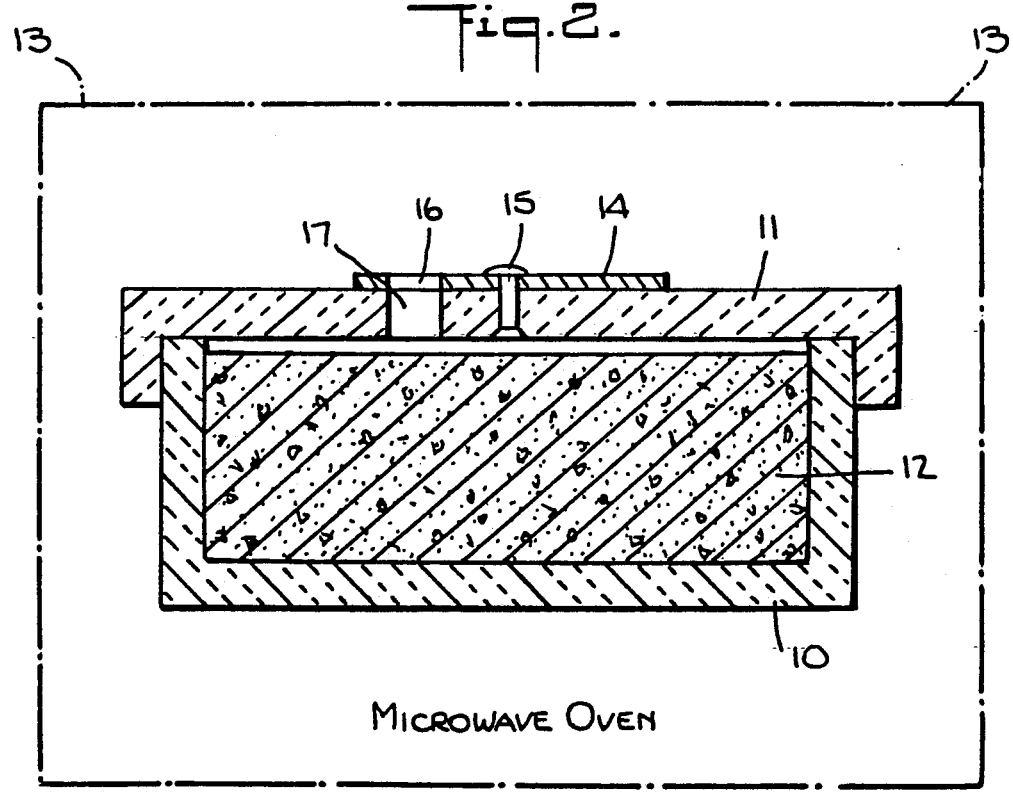
FIG. 2 is a section taken through the package which is shown in a microwave oven.
Figure 3:
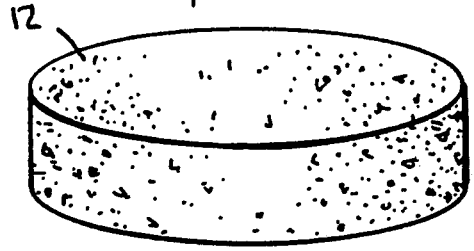
FIG. 3 is a perspective view of the porous pad housed in the container.

Referring now to the drawing, a microwave-heatable air-freshener package in accordance with the invention is constituted by a container formed of a cylindrical can 10 and a cover 11 therefor within which is housed a cylindrical porous pad 12 impregnated with a liquid fragrance. The container is molded or otherwise formed from a closed-cell foamed polyurethane, styrofoam or other rigid foam plastic material having good dielectric properties and affording good thermal insulation.

By good dielectric properties is meant that the material is permeable to microwave energy and it is not heated thereby. And by good thermal insulation is meant properties similar to that of a thermos bottle so that heat exchange through the material is very low.

As is well known, air is one of the best thermal insulators when it is entrapped, as in the closed cells of a foam plastic material. Air then prevents the flow and transfer of heat, thereby retaining heat within the container and minimizing the loss of heat from the interior to the exterior of the container. Because the thermally-insulated container is of good dielectric material, it is permeable to microwave energy.

If, therefore, the container is placed in a microwave oven, represented by block 13, the microwave energy will have no effect on the container. In a typical microwave oven, a magnetron functions to generate microwave energy at a frequency of about 1000 mHz, which energy is conveyed to a wave guide to the interior of the oven to irradiate the food, liquid or any other substance placed therein that absorbs microwave energy. This gives rise to internal molecular friction which heats up the substance at a rate that depends on its "lossy" characteristics.

Pad 12 is formed of a porous material including clay, open-cell foam plastic or any other highly porous absorbent material having electrical insulation properties so that it is more or less permeable to microwave energy and therefore only slightly heated thereby. Pad 12 is impregnated with a liquid fragrance that simulates the aroma of a natural potpourri.

The aroma of perfumes and perfume-based products such as colognes and toilets waters was originally derived from the essential oil of plants. However, since the early 19th century, chemists have succeeded in analyzing many essential oils and in creating thousands of synthetics, some simulating natural products and others yielding altogether new scents. Perfumes today are largely blends of natural and synthetic scents and of fixatives which equalize vaporization and enhance pungency. In most liquid scents, the ingredients are combined with a highly volatile alcohol carrier.

The liquid fragrance which is used in the package is one in which the scent produced, which may be entirely or only partially synthetic, simulates the aroma of a natural potpourri. The liquid fragrance does not have dielectric properties but is "lossy" and will therefore absorb microwave energy just as moist food having an oil content absorbs more microwave energy than desiccated food.

When, therefore, the package is placed in microwave oven 13 and irradiated with microwave energy, only the liquid fragrance is heated. The package is kept in the microwave oven for a period sufficient to elevate the temperature of the liquid to a level causing the liquid to volatilize to generate an aromatic vapor.

The cover 11 of the container is provided with a shutter in the form of a disc 14 of dielectric material that is rotatable on a plastic pin 15 inserted in the cover. Cover 11 has an aperture 16 therein that at a given rotary angle of the disc is in registration with vent hole 17 in the cover. Hence by turning disc 14, one can shut off vent 17, or more or less open it, and thereby control the discharge of aromatic vapor from the package.

When, therefore, the air-freshener package is in the microwave oven, the package is activated thereby, and when the package is thereafter removed from the oven and placed at a desired site in a room, an aromatic vapor will be discharged into the room at a rate determined by the shutter setting.

Because the container has good thermal insulation properties and the pad whose liquid is heated is enclosed by the container except for the small vent, the container acts to minimize the transfer of heat from the interior of the container to the exterior, and therefore to maintain the liquid at an elevated temperature for a relatively long period.

Hence while the microwave oven acts to activate the air-freshener package, the package remains in an activated state for a prolonged period when removed from the oven. If one wishes to turn off the aroma generator, it is a simple matter to do so with the shutter.

The pad acts as a reservoir for the liquid fragrance and the package is therefore not, as it were, a one-shot potpourri, for if the package is used in its active state for one-half hour or more and then turned off, it can be activated the next day or any other time, by returning the package to the microwave oven. The package contains no water or other fluid that can spill out of the package, for the liquid fragrance is fully absorbed by the porous pad.

It only takes a few minutes to activate the package in a typical microwave oven, but there is no problem in handling the package, for the exterior thereof always remains cool, and it is only the inner chamber that is hot.

In practice, the container need not be cylindrical but can be given any sculptured or contoured shape to render it attractive in a room setting. And the foam plastic container can be provided with a thin film facing sheet laminated thereto which is colored or decorated with flowers.

In practice, a user can stock a large number of the packages, and when the occasion arises, say, a festive party at home, the consumer can quickly activate several packages at a time in the kitchen microwave oven, and then distribute the activated package in various rooms, and thereby transform the environment of the home.

While there has been has been shown and described a preferred embodiment of a micro-wave heatable air-freshener package in accordance with the invention, it will be appreciated that many changes and modifications may be made therein without, however, departing from the essential spirit thereof. Thus instead of the shutter shown, use may be made of a peel-off adhesive tab covering the vent hole in the cover. And the fragrance used need not be that of a potpourri but any pleasing or stimulating fragrance that freshens the air. Also, the fragrance which impregnates the porous pad need not be in liquid form, but may be incorporated in a solid wax or other material which coats the fibers of the pad and which when rendered molten by microwave energy, releases the fragrance.

I claim:

1. An air-freshener package activated by microwave energy, said package comprising:
   (a) a rigid container whose walls are formed of thermal insulation material having dielectric properties permeable to microwave energy, and having a vent therein; and
   (b) a porous pad of dielectric material permeable to microwave energy housed in the container and impregnated with a liquid fragrance which is responsive to microwave energy whereby when the package is irradiated in a microwave over for a relatively short period of time, the liquid fragrance is heated to an elevated temperature to generate an aromatic vapor which when the package is thereafter removed from the oven and placed in a room, is discharged through the vent into the atmosphere, the thermally insulated container maintaining said liquid fragrance at said elevated temperature for a prolonged period after the package is removed from the oven.

2. A package as set forth in claim 1, wherein said container is formed by a cylindrical can and a cover therefor having said vent therein.

3. A package as set forth in claim 1, wherein said container is formed of closed cell foam plastic material.

4. A package as set forth in claim 1, wherein said material is styrofoam.

5. A package as set forth in claim 1, wherein said pad is formed of porous clay.

6. A package as set forth in claim 1, wherein said fragrance simulates the aroma of a natural potpourri.

7. A package as set forth in claim 1, further including an adjustable shutter formed of dielectric material for said vent.

* * * * *